(12) United States Patent
Van Koppenhagen et al.

(10) Patent No.: US 6,337,130 B1
(45) Date of Patent: Jan. 8, 2002

(54) ACID-TRIGGERED RELEASE MICROCAPSULES

(75) Inventors: Juanita Elena Van Koppenhagen, Vallejo; Herbert Benson Scher, Moraga; Kuo-Shin Lee, deceased, late of El Cerrito, all of CA (US), by Chi Chang Lee, legal representative; Ian Malcolm Shirley, Binfield (GB); Philip Wade, Runcorn (GB); Richard Follows, Astley (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/363,571

(22) Filed: Jul. 29, 1999

Related U.S. Application Data

(60) Provisional application No. 60/109,794, filed on Jul. 30, 1998.

(51) Int. Cl.$^7$ .............................. B32B 15/02; A61K 9/14
(52) U.S. Cl. .................. 428/402.21; 528/230; 528/245; 528/259; 528/59; 528/61; 528/65; 428/402.24; 424/78.08; 424/78.36; 424/78.37; 424/462; 424/489; 424/497; 424/405; 504/116; 504/148; 504/189
(58) Field of Search ................................. 528/230, 245, 528/259, 59, 61, 65; 428/402.21, 402.24; 424/78.08, 78.36, 78.37, 462, 489, 497, 405; 504/116, 148, 189

(56) References Cited

U.S. PATENT DOCUMENTS

| | | | |
|---|---|---|---|
| 4,766,037 A | 8/1988 | Watanabe et al. | 428/402.21 |
| 5,023,080 A | 6/1991 | Gupta | 424/405 |
| 5,441,732 A | 8/1995 | Hoeg et al. | 424/78.04 |
| 5,750,126 A | 5/1998 | Smith et al. | 424/405 |

FOREIGN PATENT DOCUMENTS

| | | |
|---|---|---|
| EP | 0 780 154 A1 | 6/1997 |
| EP | 0 823 993 A2 | 2/1998 |
| EP | 0 823 993 A3 | 4/1998 |
| GB | 2 280 164 B | 1/1995 |

OTHER PUBLICATIONS

E. Schmitz and I. Eichhorn, Acetals and hemiacetals, Chapter 7, The Chemistry of the Ether Linkage 309–351 (1967).
G. Petrov et al., Polyacetalurethanes: their synthesis, and certain properties, 11 International Polymer Science and Technology 16–18 (1984).
B. Xu, et al., Structure–Property Relationships in Thermoplastic Elastomers III. Segmented Polyacetal–Polyurethanes, 31 Journal of Applied Polymer Science 123–133 (1986).
J. Heller et al., Preparation Of Polyacetals By The Reaction Of Divinyl Ethers And Polyols, 18 Journal of Polymer Science: Polymer Letters Edition 293–297 (1980).
V. Pchelintsev, et al., Kinetic Principles and Mechanisms of Hydrolytic Degradation of Mono–and Polyacetals —A Review, 21 Polymer Degradation and Stability 285–310 (1988).
E. Schacht et al., Polymeric Pesticides, 179 Makromol. Chem. 543–548 (1978).
V. Pchelintsev et al., Molecular Structure Hydrostability and Stabilization of Polyurethane Acetals, 18 Polymer Degradation and Stability, 261–268 (1987).
V. Pchelintsev et al., Molecular Structure and Hydrolytic Stability of Polyurethane Acetals, 29 Polymer Science USSR, 1076–1081 (1987).

*Primary Examiner*—Samuel A. Acquah
(74) *Attorney, Agent, or Firm*—Townsend and Townsend and Crew LLP

(57) ABSTRACT

Microcapsules of a microcapsule formed of a polyurea shell wall and an encapsulated ingredient or ingredients enclosed within the wall, the wall comprising at least one oligomeric acetal having the moiety

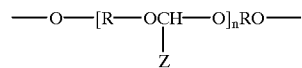

in which R is (a) a moiety containing a chain of from 5 to about 40 optionally substituted carbon atoms, (b) a moiety containing a chain of from 4 to about 40 carbon atoms and one or more internally linked oxygen or sulfur atoms or —NH-groups, or (c) an optionally substituted ethylene or propylene moiety Z is (a) an optionally substituted phenyl group, (b) an optionally substituted $C_1$–$C_{20}$ alkyl, $C_2$–$C_{20}$ alkenyl, $C_3$–$C_8$ cycloalkyl or $C_5$–$C_8$ cycloalkenyl group, or (c) benzoyl, and n is 1 if R is (a) or (b), or is 2–20 if R is (c). The microcapsules are acid-sensitive and the capsule walls are relatively readily degraded or disintegrated by contacting the microcapsules with an acidic substance, preferably an organic or inorganic acid whereby the encapsulated ingredient or ingredients are released into the surrounding environment. The invention is particularly suitable for encapsulation of biologically active substances and agrochemicals, and most preferably pesticides for foliar treatment.

21 Claims, No Drawings

ACID-TRIGGERED RELEASE MICROCAPSULES

This application claims the benefit of provisional application No. 60,109,794, filed Jul. 30, 1998.

This invention pertains to certain microencapsulated compositions which contain an ingredient or ingredients encapsulated within a polymeric shell wall, particularly a polyurea shell wall, in which the shell wall contains one or more oligomeric unit sensitive to acidic conditions, as well as processes for the production of such microcapsules, and methods for their use. The oligomeric unit(s) enable(s) triggering of the release of the encapsulated contents on exposure of the capsules to acidic conditions.

The microcapsules of this invention have been found especially suitable for use in producing encapsulated formulations of pesticides, for both agricultural and non-agricultural use. They are also suitable for use in encapsulated formulations of non-pesticidal agricultural chemicals such as plant growth regulators, insect growth regulators, fertilizers, and other agriculturally useful materials. In addition, they are useful for encapsulation of materials outside the agricultural field such as encapsulation of paint biocides for controlled release into paint films under mildly acidic conditions.

In many instances, particularly in agriculture, the object of producing microencapsulated compositions has been to provide controlled release of the encapsulated active ingredient, and particularly to provide a release for longer term efficacy so that the active ingredient is released over a period of time and is available throughout the effective period. This is particularly significant for pesticides or other biologically active ingredients which are degraded or decomposed over a relatively short period of time or under certain environmental conditions. Use of microencapsulated compositions in these situations provides effective activity of the encapsulated ingredient over a longer period of time since it will be released continuously into the environment in the amount needed rather than in one large initial dose.

Currently, microencapsulated pesticides are used primarily as preemergence pesticides, that is, they are applied to soil prior to the emergence of vegetation or the appearance of insects, so that they are available to kill or control newly emerged weed species or insects in their larval stages. Again, in those applications, relatively slow release rates are desired so that the pesticide is released into the environment over a period of time, usually over at least several weeks.

Microencapsulated formulations for quick release are known in a number of other applications, such as the printing and xerography industries, in which materials such as inks, pigments, toner particles, etc., are microencapsulated and released quickly upon application of physical force or heat. Rapid or quick release microcapsules could have utility in agriculture in situations in which controlled release is not desired, but microencapsulation of the active ingredient is desired for any of a number of reasons. For example, microencapsulation can be desired to protect against dermal toxicity effects of pesticides during their handling (for instance, production, storage or loading into spray equipment). However, a quick release of the pesticide may be desired in order to make the pesticide immediately available to control a pest, as is usually the case with nonencapsulated or non-controlled release formulations such as solutions, emulsions, dusts, powders, granules, etc. Another instance in which it is desirable to have encapsulation but quick release of a pesticide is in the production of pesticidal products containing two active ingredients which may be reactive with each other or otherwise incompatible in a single system.

Microencapsulation of pesticides may often provide an increase in the safety of pesticide handling, to the extent that the polymer wall of a microcapsule minimizes contact of the handler with the active pesticide, particularly if the pesticide is in the form of a suspension of microcapsules. The provision of a triggered release microencapsulated formulation of a pesticide could minimize contact of a handler with the active pesticide, yet provide the necessary quick release of the active ingredient when applied to protect plants from an insect pest which is already present or about to invade. Additionally, triggered release encapsulated products containing pyrethroids could be useful in industrial, commercial or residential pest control.

SUMMARY OF THE INVENTION

This invention provides acid-triggered or -sensitive microcapsules which satisfy the above-mentioned objectives.

In one aspect, this invention comprises a microcapsule formed of a polyurea shell wall and an encapsulated ingredient or ingredients enclosed within the wall, the wall comprising at least one acid-sensitive oligomeric acetal moiety. In a preferred embodiment the acetal moiety as present in the capsule wall has the formula

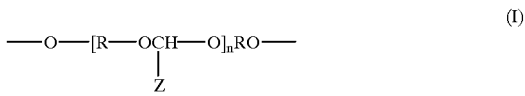

(I)

in which
R is (a) a moiety containing a chain of from 5 to about 40 optionally substituted carbon atoms, (b) a moiety containing a chain of from 4 to about 40 carbon atoms and one or more internally linked oxygen or sulfur atoms or —NH— groups, or (c) an optionally substituted ethylene or propylene moiety;

Z is (a) an optionally substituted phenyl group, (b) an optionally substituted $C_1$–$C_{20}$ alkyl, $C_2$–$C_{20}$ alkenyl, $C_3$–$C_8$ cycloalkyl or $C_5$–$C_8$ cycloalkenyl group or (c) benzoyl; and n is 1 if R is (a) or (b), or is 2–20 if R is (c).

In another aspect, this invention comprises a process for the production of such microcapsules comprising the steps of (a) reacting an oligomeric acetal with a diisocyanate having the formula OCN—$R_1$—NCO in which $R_1$ is an aliphatic or aromatic moiety to produce a prepolymer and (b) utilizing the product of (a) as the prepolymer in a polyurea microencapsulation process. In a preferred embodiment the prepolymer contains a moiety having the formula

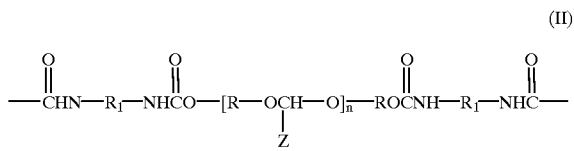

(II)

in which R, R1 and Z are as described above.

DETAILED DESCRIPTION OF THE INVENTION

This invention relates to microcapsules which contain encapsulated material and which are sensitive to the presence of acid, and on exposure to an acidic environment break down and/or become porous so as to release the encapsulated substance into the surrounding environment.

The microcapsules are characterized by having shells formed of polyurea and containing an oligomeric acetal moiety. By oligomeric acetal moiety is meant a moiety which contains one or more in-chain acetal linkages and which has functional groups, preferably at the ends of the chain, which may be reacted with other materials such that the oligomeric acetal may be incorporated into a microcapsule wall. Oligomeric acetals may be made by a number of methods known to those skilled in the art, for example, by co-polymerization of diols and aldehydes, by co-polymerization of diols and divinyl ethers, and by homo-polymerization of aldehydes. In general, oligomeric acetals are characterized by having a group of the general formula

$$HO-[CHX-O]_mH \quad (III)$$

in which the identity of X depends on the nature of the reactants and reactions utilized to produce the acetals.

Preferred acetals for use in the microcapsules of this invention are those having the formula

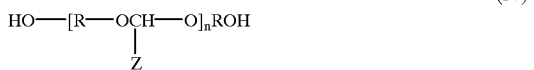
$$HO-[R-OCH(Z)-O]_nROH \quad (IV)$$

in which
R is (a) a moiety containing a chain of from 5 to about 40 optionally substituted carbon atoms, (b) a moiety containing a chain of from 4 to about 40 carbon atoms and one or more internally linked oxygen or sulfur atoms or —NH— groups, or (c) an optionally substituted ethylene or propylene moiety; Z is (a) an optionally substituted phenyl group, (b) an optionally substituted $C_1$-$C_{20}$ alkyl, $C_2$-$C_{20}$ alkenyl, $C_3$-$C_8$ cycloalkyl or $C_5$-$C_8$ cycloalkenyl group, or (c) benzoyl; and
n is 1 if R is (a) or (b), or is 2–20 if R is (c).

Acetals produced by co-polymerization of diols and divinyl/ethers have moieties of the general formula

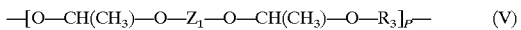
$$-[O-CH(CH_3)-O-Z_1-O-CH(CH_3)-O-R_3]_p- \quad (V)$$

in which $Z_1$ represents a group bridging two vinyl ether moieties, and $R_3$ represents the skeleton of the diol.

Acetals produced by homopolymerization of aldehydes have moieties of the general formula

$$-[CHOR_4-O]_q \quad (VI)$$

in which $R_4$ represents the portion derived from an aldehyde $R_4CHO$.

As will be described below, the microcapsules are prepared by a process in which the oligomeric acetal (previously prepared) is incorporated into a diisocyanate prepolymer which is then converted to a polyurea, typically by an interfacial polymerization process. In a preferred embodiment the acetal has the formula

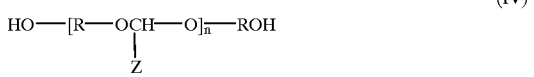
$$HO-[R-OCH(Z)-O]_{\overline{n}}-ROH \quad (IV)$$

in which R and n are as described above and the oligomeric acetal units which are contained in the polyurea capsule walls have the corresponding formula

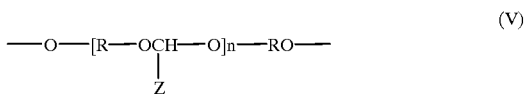
$$-O-[R-OCH(Z)-O]_n-RO- \quad (V)$$

If the capsules are not in an acidic environment, or are in an environment only weakly acidic, they function as typical controlled diffusion release polyurea microcapsules, permitting release of the encapsulated substance into the surrounding area in a controlled manner which is determined primarily by wall characteristics of the polyurea shells such as thickness, capsule size, permeability, etc. If, on the other hand, the capsules are placed in an acidic environment in which the pH is between about 0.5 and about 5, preferably between about 1 and about 3), for instance are in the presence of, or are contacted with, an acidic substance of nature and/or in an amount which results in the pH of the environment being at a value of between about 0.5 and about 5, preferably about 1 and about 3, and in which sufficient water is present, the acetal moieties in the capsule wall hydrolyze relatively rapidly so that the overall capsule wall, now missing a significant link in the structure, becomes porous, triggering the release of the encapsulated material. Depending on the nature of the wall (including the nature and relative quantity of hydrolyzable acetal moieties, and the pH of the environment, the release may be relatively quick. What is effected by the contact of the capsules with an acidic environment is not necessarily a quick release but a substantial increase in the release rate. Capsules of this invention may be designed to give relatively quick release if that is desired.

The encapsulated material may be any type of material for which capsules of this type are suitable. Preferably the encapsulated material is comprised of a liquid; that is, it may be in the form of a liquid itself, or in the form of a solid which is suspended or dissolved in a liquid, a mixture of liquids which are dissolved one in the other, or a liquid emulsion. For purposes of this invention, the products will be described in terms of encapsulation of agricultural or non-agricultural pesticides. However, the invention is not so limited and, as mentioned above, may be used for encapsulation of many suitable materials for many purposes.

When the encapsulated material is a biologically active substance such as a pesticide, again, it may be a single liquid active ingredient, a solid active ingredient dissolved or suspended in a liquid (in which case the liquid may be an inert material or may be a second active ingredient which is in liquid form), a mixture of liquids dissolved one in the other, or an emulsion. The encapsulated material may also contain other substances such as surfactants, dispersants and the like. If any of the materials, particularly the active ingredient, is sensitive to ultraviolet light, the encapsulated liquid material may also contain a protectant, for example, a suspended solid ultraviolet light protectant such as titanium and/or zinc oxide as described in PCT application WO 96/33611 or another known protectant such as carbon black or activated charcoal. As used herein, "biologically active ingredient" includes not only pesticides such as insecticides, herbicides, fungicides, acaricides, miticides, rodenticides and other materials which are toxic or poisonous to pests, but also chemicals having biological activity on pests such as plant and/or insect growth regulators and those having beneficial effects such as fertilizers, hormones, etc.

The preferred acetal moieties contained in the capsule walls have the general formula

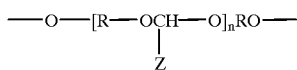

$$\text{—O—[R—OCH—O]}_n\text{RO—} \quad \text{(I)}$$
$$|$$
$$Z$$

in which
- R is (a) a moiety containing a chain of from 5 to about 40 optionally substituted carbon atoms, (b) a moiety containing a chain of from 4 to about 40 carbon atoms and one or more internally linked oxygen or sulfur atoms or —NH— groups, or (c) an optionally substituted ethylene or propylene moiety;
- Z is (a) an optionally substituted phenyl group, (b) an optionally substituted $C_1$–$C_{20}$ alkyl, $C_2$–$C_{20}$ alkenyl, $C_3$–$C_8$ cycloalkyl or $C_5$–$C_8$ cycloalkenyl group, or (c) benzoyl; and n is 1 if R is (a) or (b), or is 2–20 if R is (c).

Preferably R is a $C_5$–$C_{40}$ alkyl group or a group having the formula —$CH_2$—$R_2$—$CH_2$—. $R_2$ is optionally substituted phenyl or $C_5$–$C_{15}$ cycloalkyl or cycloalkenyl (and if $R_2$ is cycloalkenyl the group may have one or more double bonds) in which the methylene groups are substituted at least three carbons apart on the ring. If R is —$CH_2$—$R_2$—$CH_2$—, the methylene groups are no closer than at the 1- and 3-positions on the ring so that the two methylene groups together with the ring atoms of group R2 form at least a five-carbon atom chain.

In a second embodiment, R is a group or moiety containing a chain of from 4 to about 40 carbon atoms as well as one or more internally-linked oxygen or sulfur atoms or —NH— groups. In a third embodiment R is an optionally substituted ethylene or propylene moiety and n is a value from 2 to 20.

The necessity of having at least a five-carbon chain if R is (a) or at least a four-carbon chain plus an internally linked atom if R is (b) or a value of n of at least two if R is (c) is occasioned by a need to prevent internal cyclization of the acetal formed, as is known in the literature. Minimum chain links, as mentioned above, are sufficient to prevent or at least greatly minimize such undesired cyclization.

The preferred oligomers of this invention will have varying size. Preferably the number average molar mass ($M_n$), is at least about 200, preferably from about 200 to about 4000, most preferably from about 1000 to about 2000.

The group Z is preferably an optionally substituted phenyl group or an optionally substituted $C_1$–$C_{20}$ alkyl group such as tridecyl or t-butyl, an optionally substituted $C_2$–$C_{20}$ alkenyl group such as crotyl or an optionally substituted $C_3$–$C_8$ cycloalkyl group such as cyclohexyl. It could be noted that Group Z may be derived from a mono- or poly-aldehyde.

In general, ingredients for the products of this invention are chosen (among those possible) so as to exclude combinations which are reactive toward each other, except when reaction is desired. Thus the choice of oligomeric acetals, diols, aldehydes, and materials to be encapsulated is made so as to prevent undesirable reactions. In some cases, materials to be encapsulated may require neutralization or other modification so as to prevent reaction.

The acetal groups are prepared by known techniques. The preferred acetals are prepared by condensation of a diol with an aldehyde as described, for example, in Petrov et al., Kauchukei Rezina, No. 12, page 4 (1983), Pchelintsev et al., Polymer Degradation and Stability, Vol. 21, page 285 (1988) and Xu et al., J. Appl. Polymer Science, Vol. 31, page 123 (1986). The diols used to prepare the acetals of this invention are of several types. The first type is a straight or branched chain optionally substituted alpha, omega-alkanediol having from 5–40 carbon atoms. Optional substituents on the carbon atoms include alkyl and alkoxy groups. Examples of such compounds include 1,5-pentanediol, 1,8-octanediol, 1,10-decanediol, and 1,12-dodecanediol. The second type of diol is one having the general formula HO—$CH_2$—$R_2$—$CH_2$—OH in which $R_2$ is an optionally substituted $C_3$–$C_8$ cycloalkyl or $C_5$–$C_8$ cycloalkenyl group or a phenyl group and in which the methylol groups are substituted at least three carbon atoms apart on the cycloalkyl or phenyl ring. Examples of such compounds are 1,4-cyclohexanedimethanol, and 5-t-butyl-1,3-cyclohexanedimethanol.

A third type of diol is an alpha, omega alkanediol containing at least one chain of from 4 to about 40 carbon atoms and one or more internally linked chalkogen, preferably oxygen or sulfur atoms or —NH— groups. Examples of such diols are polytetrahydrofuran and polyurethanediol, H[O—$CH_2CH_2$O—CONH—($CH_2$)$_6$NHCO]$_n$—O$CH_2CH_2$—OH. Another type of diol useful herein is the polyalkylene glycols having 2–3 carbon alkylene groups. Examples of such glycols include diethylene, triethylene, tetraethylene, dipropylene and pentaethylene glycols.

The aldehydes useful in the practice of this invention include optionally substituted aromatic and aliphatic aldehydes. Optional substituents include halogen, nitro, and haloalkyl. Unsaturated aldehydes may be utilized providing the unsaturated moiety does not react with the material to be encapsulated or other ingredients of the final encapsulated composition. Preferred aldehydes are optionally substituted benzaldehyde and $C_1$–$C_{12}$ alkyl aldehydes. Preferred reactants to produce the acetals of this invention are, for the diol, $C_8$–$C_{12}$ alkanediols, and for the aldehyde, an optionally substituted benzaldehyde.

In general, the production of the oligomeric acetal from the diol and aldehyde is carried out at a temperature of between about 50 and about 140° C., generally in a solvent such as toluene or xylene under reflux, and in the presence of a catalyst, particularly p-tolulenesulfonic acid. Other suitable catalysts for the reaction are sulfuric and trichloroacetic acids. Ratios of diol to aldehyde are from about 1:1 to about 5:1 preferably from about 1.1:1 to about 1.3:1. The reaction is continued until the appropriate or calculated quantity of water has been removed by azeotropic distillation. Work-up procedures for the reaction product and recovery of the oligomeric acetal generally depend on the nature of the reagents but usually involve washing the resulting solution with dilute base (e.g., sodium carbonate) to remove the acid catalyst followed by washing with water, drying, filtering and evaporating the solvent. Unreacted aldehyde may be removed from the oligomer by customary techniques such as trituration.

Other types of acetals which may be used in this invention are prepared as follows:

Copolymerization of diols and divinyl ethers can be represented by the reaction

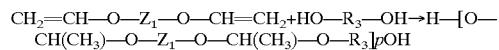

$$CH_2=CH—O—Z_1—O—CH=CH_2+HO—R_3—OH \rightarrow H—[O—CH(CH_3)—O—Z_1—O—CH(CH_3)—O—R_3]_p OH$$

This reaction is known in the literature, for instance in Heller, et al., J. Polymer Science, Polym. Lett. Edn. 18, 193 (1980), which describes polymers having molecular weights between 33,000 and 200,000.

Homopolymerization of aldehydes proceeds according to the reaction

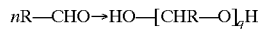

$$nR—CHO \rightarrow HO—[CHR—O]_q H$$

The reaction is known in the literature, for instance in Kubica et al.; Polymer, 21, 1433 (1980).

However produced, the oligomeric acetal is then utilized as one of the materials in producing polyurea microcapsules such that the walls of the resulting capsules contain oligomeric acetal units or moieties. In one embodiment the capsule walls will contain two or more different types of oligomeric acetals having different hydrolysis rates. The suitability of oligomeric acetals for inclusion in microcapsules according to this invention can readily be determined by assessing two properties—their stability in the presence of bases and their hydrolyzability in the presence of acidic materials, i.e., at a pH of from about 0.5 to about 5, preferably from about 1 to about 3.

Hydrolyzability in the presence of acids is readily determined by using a procedure such as that described in Example 8 below. Stability towards bases is readily determined by utilization of a similar procedure, employing a base rather than an acid. The rate of hydrolysis is generally dependent on the nature of the oligomer and of the acid used.

There are a number of known techniques for producing polyurea microcapsules which contain an encapsulated ingredient (usually in liquid form) enclosed within a polymeric shell wall. A main technique is producing an oil-in-water emulsion which contains one or more monomers or prepolymers, then causing interfacial polymerization to occur, so as to form microcapsules of polymer enclosing the (other) contents of the oil phase droplets. Two major types of such interfacial polymerization are the Zeneca process, in which monomers exist only in the organic (oil) phase, and another process, described in patents of various companies, such as Monsanto and Novartis, in which monomers are contained in both the organic and aqueous phase.

In the Zeneca process, as described in U.S. Pat. No. 4,285,720, the disclosure of which is hereby incorporated herein by reference, two liquid phases are produced—an aqueous phase containing water, one or more surfactants, and a protective colloid, and an organic phase which comprises the material to be encapsulated, optionally one or more solvents, and one or more organic polyisocyanates. Either the material to be encapsulated or the solvent may also serve as a solvent for the polyisocyanate or polyisocyanates.

An oil-in-water emulsion of the two phases is then prepared at high shear. The emulsion is then stirred under low shear and maintained at a temperature range of from about 20° C. to about 90° C., during which hydrolysis and reaction occur involving the organic isocyanate or isocyanates to form a polyurea at the interfaces between the droplets of the organic phase and the aqueous phase. Adjustment of the pH of the resulting mixture and the temperature range during this stage advance this condensation reaction.

The aqueous phase is prepared from water, a protective colloid, and preferably a surfactant. In general, the surfactant or surfactants in this phase may be anionic or nonionic surfactants with an HLB range of from about 12 to about 16. If more than one surfactant is used, individual surfactants may have HLB values lower than 12 or higher than 16 as long as the overall HLB value of the combined surfactants will be within the range of about 12–16. Suitable surfactants include polyethylene glycol ethers of linear alcohols, ethoxylated nonylphenols, naphthalene sulfonates, salts of long chain alkylbenzene sulfonates, block copolymers of propylene and ethylene oxides, anionic/nonionic blends, and the like. Preferably the hydrophobic portion of the surfactant has chemical characteristics similar to the water-immiscible phase. Thus, when the latter contains an aromatic solvent, one suitable surfactant would be an ethoxylated nonylphenol. Particularly preferred surfactants include block copolymers of propylene and ethylene oxides, and anionic/nonionic blends.

The protective colloid present in the aqueous (or continuous) phase must absorb strongly onto the surface of the oil droplets and can be selected from a wide range of such materials including polyacrylates, methyl cellulose, polyvinyl alcohol, polyacrylamide, poly (methylvinyl ether/maleic anhydride), graft copolymers of polyvinyl alcohol and methylvinyl ether/maleic acid (hydrolyzed methylvinyl ether/maleic anhydride (see U.S. Pat. No. 4,448,929, the disclosure of which is hereby incoporated by reference herein)] and alkali metal or alkaline earth metal lignosulfonates. Preferably, however, the protective colloid is selected from alkali metal and alkaline earth metal lignosulfonates, most preferably sodium lignosulfonates.

The range of surfactant concentration (when a surfactant is used) in the process is from about 0.01 to about 3.0 percent by weight, based on the aqueous phase, but higher concentrations of surfactant may also be used. The protective colloid is generally present in the aqueous phase in an amount of from about 1.0 to about 5.0 percent by weight, based on the aqueous phase. The amount of protective colloid employed will depend on various factors, such as molecular weight, compatibility, etc., so long as enough is present to completely coat the surfaces of all the oil droplets. The protective colloid can be added to the aqueous phase prior to the addition of the organic phase, or can be added to the overall system after the addition of the organic phase or the dispersion of it. The surfactants should be chosen so as to not displace the protective colloid from the droplet surfaces.

The organic phase comprises a water immiscible biologically active ingredient such as a pesticide and/or other material to be encapsulated, optionally one or more solvents and one or more (aromatic) di- and/or polyisocyanates. Preferably it includes an aromatic diisocyanate and preferably ultimately also an aromatic polyisocyanate having three or more isocyanate groups. Suitable solvents include aromatic hydrocarbons such as xylenes, naphthalenes, or mixtures of aromatics; aliphatic or cycloaliphatic hydrocarbons such as hexane, heptane and cyclohexane; alkyl esters including alkyl acetates and alkyl phthalates, ketones such as cyclohexanone or acetophenone, chlorinated hydrocarbons, vegetable oils, or mixtures of two or more such solvents.

Diisocyanates usable in this process include m-phenylene diisocyanate, p-phenylene diisocyanate; 1-chloro-2,4-phenylene diisocyanate; 4,4'-methylenebis (phenyl isocyanate); 3,3'-dimethyl-4,4'-biphenylene diisocyanate, 4,4'-methylenebis (2-methylphenyl isocyanate); 3,3'dimethoxy-4,4'-biphenylene diisocyanate; 2,4-tolylene diisocyanate; 2,6-tolylene diisocyanate, isomeric mixtures of 2,4- and 2,6-tolylene diisocyanate and 2,2', 5,5'-tetramethyl-4,4'-biphenylene diisocyanate. Also usable in this process are aliphatic diisocyanates such as isophorone diisocyanates and hexane-1,6-diisocyanate.

Aromatic polyisocyanates having 3 or more isocyanate groups include polymethylene polyphenylisocyanate (available from ICI or Bayer), triphenylmethane triisocyanate ("Desmodur R") and the adduct formed between 1 mole of trimethylolpropane and 3 moles of tolylene diisocyanate ("Desmodur TH") (Desmodur products are available from Bayer A. G.).

In the second type of process, aqueous and organic phases are similarly prepared. However, whereas in the Zeneca process hydrolysis of the isocyanate or isocyanates occurs to form the corresponding amine (which is then reacted with the isocyanate), in this process the aqueous phase further contains a water-soluble amine which is different from the amine produced by hydrolysis of the isocyanate, and which reacts with the isocyanate or isocyanates to form the polyurea shell wall. A particularly preferred amine in this process is hexamethylenediamine. Processes of this type are described, for instance, in U.S. Pat. Nos. 4,280,833 and 4,938,797, the disclosures of which are hereby incorporated herein.

Whichever process is utilized to produce the polyurea microcapsules, the acetal is introduced into the process by first reacting it with the (aromatic) diisocyanate to form an acetal-containing prepolymer. Preferably the prepolymer is comprised predominantly of molecules having the formula

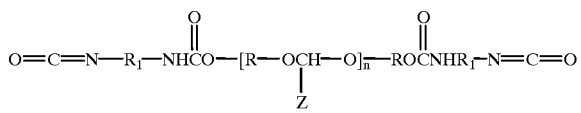

and/or comprising small oligomers of it, which have up to about 10 units of the formula (II)

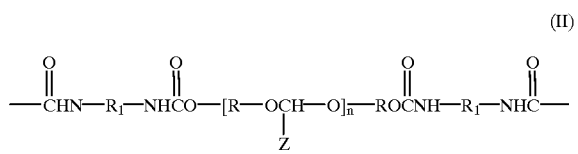

in which R, $R_1$ and Z are as previously defined.

The production of this prepolymer is generally carried out at temperatures of from about 45 to about 60, preferably from about 50 to about 55° C. Reaction times generally range from 20–70 minutes, preferably 50–60 minutes. The oligomeric acetal is employed in a mole ratio with regard to the aromatic diisocyanate of from about 1:2 to about 1:20, preferably from about 1:3 to about 1:5. Excess isocyanate is needed to prevent further oligomerization of the acetal-containing prepolymer.

The acetal-containing prepolymer thus formed may be used directly in the microencapsulation step.

If a version of the Zeneca process is utilized which involves including both an aromatic diisocyanate and an aromatic polyisocyanate having three or more isocyanate groups, then the oligomeric acetal is first reacted with the diisocyanate to form the prepolymer and the polyisocyanate is then added to the organic phase. Presence of the polyisocyanate during the formation of the acetal-diisocyanate prepolymer is not desirable as it could result in undesirable cross-linking and joining before the capsule wall formation step.

Whether the Zeneca or another process is utilized, the resulting product is an aqueous suspension of the microcapsules in which the non-wall-forming material in the organic phase is contained within the microcapsules. The aqueous phase of the suspension contains those adjuvants and other materials which were present in the aqueous phase of the emulsion (except for monomers originally present).

The microcapsule suspensions thus produced may be utilized in the normal fashion of such products, i.e., by packaging the suspension and ultimately transferring the suspension into a spray tank or other spray equipment in which it is mixed with water to form a sprayable suspension. Alternatively, the aqueous suspension of microcapsules may be converted into a dry microcapsule product by spray drying or other known techniques and the resulting material packaged in dry form.

To take advantage of the acid sensitivity of the microcapsules due to the presence of the oligomeric acetal moiety, for use the capsules are put into contact with an acidic substance. Most commonly this will be accomplished by adding an acidic substance to the spray tank or spray equipment containing the microcapsules and water so that release of the encapsulated material can begin in the spray tank. In one convenient aspect of the invention, the microcapsules (either in suspension or dry form) are packaged with, but separately from, a suitable acidic substance in any of a number of forms generally known as "twin packs" so that the acidic substance is conveniently on hand, in an appropriate amount, for use in this way.

For use in paint films, biocides or fungicides may be encapsulated in the microcapsules of the present invention and supplied as a concentrate which may be admixed in an appropriate dose immediately prior to use with carboxylic acid-containing paint latexes which have been adjusted to about pH 8 with ammonia. Upon casting and film formation the water and ammonia will evaporate. Depending upon the carboxylic acid content and the type of initiators used to make the latex the pH of the paint film may fall to about 5. Slow hydrolysis of the acetal at this pH results in the release of the biocide or fungicide into the film.

The acidic substance may be any of a number of acids or acidic substances and is utilized in an amount so as to provide a resulting pH in the presence of the acid-sensitive microcapsules of from about 0.5 to about 5, preferably from about 1 to about 3. Preferred acids are p-toluenesulfonic acid, sulfuric acid, and other organic or inorganic acids such as hydrochloric, trichloroacetic, oxalic, picric, formic and nitric.

The acid may be introduced so as to either directly or indirectly provide an environment in which the pH is from about 0.5 to about 5, preferably from about 1 to about 3 (in the presence of the capsules). In the direct method, the acid is added in an amount so as to provide an environment within the aforesaid pH range at or close to the time of addition of the acid, e.g. in the spray tank. However, after spraying such a product, the pH of the sprayed droplets will naturally decrease due to an increased concentration of acid as the water evaporates. Accordingly, in an indirect method the amount of acid utilized in this invention may be less than that which will provide an immediate or near-immediate pH of from 0.5 to about 5 (preferably from about 1 to about 3), but which is sufficient to provide such a pH after spraying as the sprayed water evaporates. In general, establishment of a pH in the spray tank as high as about 4–6 would result in the pH of the environment (e.g., water droplet on plant surfaces) decreasing to a value of from about 1 to about 3 as the water evaporates. Thus, the concept of this invention includes initially contacting the microcapsules with an acidic substance in a spray tank or similar apparatus such that the initial environment is at a pH value of as high as about 6, then spraying or otherwise applying the resulting dispersion to foliage or other surfaces. In such an application the pH will drop as water evaporates to a preferred target value of from about 1 to about 3.

Alternatively, the microcapsules may be sprayed without utilizing acid, in which case they would function as diffusion controlled release capsules, slowly releasing the contained ingredient into the surrounding environment. Under these conditions the rate of release is controlled by particle size, wall thickness, and the permeability of the wall.

Another method of introducing acid is to co-encapsulate a masked acid such as a cationic photo-initiator with the contents of the micro-capsule. The acid is generated by exposure to another condition such as ultraviolet light. The released acid may then cleave acid sensitive moieties built into the wall, for example silyl ether or silylureido bonds as described in U.S. Pat. No. 4,766,037.

Biological effects of the encapsulated product can be enhanced by use of a humectant such as polyethylene glycol, glycerol or polyvinyl alcohol with the final product.

One of the advantages of the microcapsules of this invention is that they provide the possibility of producing a comparatively safer pesticidal product as compared to standard liquid or solid products but still provide the ready availability of the encapsulated material for pest control.

For example, pyrethroid insecticides are known in some cases to provoke an adverse skin reaction. This reaction has been described as a burning, tingling, numbing or prickling sensation, which is most pronounced on regions of the handler's face. This reaction, known as paraesthesia, is generally associated with transfer of trace amounts of the pyrethroid to the handler's face through inadvertent touching by a contaminated hand. In current agricultural practices, compositions containing pyrethroids for application to plant foliage are provided in nonencapsulated forms, such as emulsifiable concentrates, wettable powders and dusts.

Microencapsulation of pesticides utilizing the current invention may provide an increase in the safety of pesticide handling to the extent that the polymer wall of the microcapsule minimizes contact of the handler with the active pesticide. The quick release properties of the compositions of this invention enable the active ingredient to be delivered into the environment in relatively the same concentration and with relatively the same effect as a typical nonencapsulated composition. This avoids typical drawbacks of diffusion controlled release microcapsules which are not satisfactory when a relatively complete and quick release of the encapsulated ingredient is needed.

The invention may be used to produce capsule suspensions containing two materials, for instance two herbicides, which may be incompatible with each other, with one material being encapsulated and the other contained in the aqueous phase. These compositi4ons are storage-stable but produce a combination herbicidal product in the spray tank when acid substance is added, so that both herbicides may be applied together.

The invention is further illustrated by the following examples:
Preparation of Oligomeric Acetals

EXAMPLES 1–7

The following method was used to prepare the acetals from the materials listed in the following Table 1. A mixture of the indicated quantity of the diol, the aldehyde and p-toluenesulfonic acid catalyst in toluene or xylene was heated under reflux. The reaction was continued until the appropriate or calculated quantity of water had been removed by azeotropic distillation. Work-up was done according to the nature of the reagents, e.g., by washing the reacted toluene or xylene solution with dilute sodium carbonate solution to remove the p-toluenesulfonic acid followed by washing with water. After drying and filtering, the solvent was evaporated under reduced pressure, leaving the crude oligomer. If desired, unreacted aldehyde was removed by trituration with hexane.

TABLE 1

| Example | Diol, mmol | Aldehyde, mmol | Catalyst, mg. |
| --- | --- | --- | --- |
| 1 | DD, 56 | BA, 47 | 30 |
| 2 | CHD, 52 | BA, 45 | 30 |
| 3 | DEG, 197 | BA, 172 | 21 |
| 4 | TEG, 54 | BA, 45 | 50 |
| 5 | DD, 50 | CIN, 50 | 60 |
| 6 | DD, 37 | PGLY, 38 | 70 |
| 7 | DD, 37 DEG, 7 | BA, 62 | 30 |

Key
OD = 1,8-octanediol; DD = 1,10-decanediol; CHD = cyclohexane-1,4-dimethanol; DEG = diethylene glycol; TEG = triethylene glycol; BA = benzaldehyde; CIN = cinnamaldehyde; PGLY = phenylglyoxal

EXAMPLE 8
Hydrolysis of Oligomeric Acetals

Oligomeric acetals prepared as above were subjected to acid hydrolysis by the following method: A solution of the acid in water is added to the oligomer. The resulting two-phase system is intimately mixed using a vibrator. After a given time a cloudy emulsion with the oligomer as the continuous phase, is usually obtained. Significant hydrolysis and/or disappearance of cloudiness is shown by a decrease in the viscosity of the mixture. Samples may be withdrawn from the mixture at given times and analyzed by IR or NMR spectroscopy. The following Table 2 is a summary of hydrolysis of the oligomeric acetals utilizing different acids and different values for pKa.

TABLE 2

| Oligomer Type | Mn | Catalyst type | pKa | wt %* | molarity | Hydrolysis % (approx.) | Time |
| --- | --- | --- | --- | --- | --- | --- | --- |
| DEG-BA | 810 | TsOH | | 1.0 | 0.3 | 100 | <2 min. |
| DBG-BA | 721 | PA | 0.38 | 1.6 | 0.4 | 100 | <5 min. |
| DEG-BA | 802 | HCl | | 0.3 | 0.05 | 100 | 6 min. |
| DEG-BA | 810 | TCA | 0.7 | 1.1 | 0.4 | 100 | 14 min. |
| DEG-BA | 721 | THBA | 1.68 | 0.2 | 0.1 | 100 | 40 min. |
| DEG-BA | 721 | OA | 1.23(1) 4.192) | 0.2 | 0.1 | 100 | 50 min. |
| DEG-BA | 721 | AA | 4.75 | 0.5 | 0.1 | 20 | 24 hours |
| DEG-BA | 721 | TPS | | 0.8 | 0.2 | <5 | 24 hours |
| DEG-BA | 810 | NaOH | | 26.0 | "45" | 0 | 24 hours |
| DEG-BA | 810 | TCA | 0.7 | 1.1 | 0.4 | 100 | 14 min. |
| DDOD-BA | 2,780 | TCA | 0.7 | 1.2 | 0.4 | 100 | 45 min. |

Key:
PA = Picric Acid;
TCA = Trichloroacetic Acid;
THBA = Trihydroxybenzoic Acid;
OA = Oxalic Acid;
AA = Acetic Acid;
TPS = Triphenylsilanol;
TSOH = P-Toluenesulfonic Acid;
DDOD-BA = oligoacetal made from mixture of BA, DD and OD Preparation of Microcapsules The following examples 9–16 represent the reaction between toluene diisocyanate, as a representative aromatic diisocyanate, and oligomeric acetals to produce a prepolymer, followed by forming microcapsules. The active ingredient which was encapsulated was, as indicated, one of two herbicides—butylate [BUT], (S-ethyl diisobutyl thiocarbamate) or fluazifop-P-butyl [FPB], (R)-2-[4([5-(trifluoromethyl)-2-pyridinyl]oxy)phenoxy] propanoate.

A solution of a dry or a dewatered oligomeric acetal and dibutyltin dilaurate (10 mg.) in the herbicide (half the amount indicated in Table 3) was added drop-wise to a solution of toluene diisocyanate (TDI) in the remaining herbicide. The solution of oligomeric acetal was added at such a rate as to keep the temperature of the reaction mixture between 20–25° C. In some experiments polymethylene polyphenylisocyanate (PMPI) was also utilized, to provide cross-linking in the microcapsule walls. In those experiments, the PMPI was added to the organic phase only after formation of the prepolymer between oligomeric acetal and TDI occurred, so as to prevent premature cross-linking and possible gelling.

The prepolymer was then used to prepare microcapsules containing the herbicide by the following procedure:

The oil phase was added to the aqueous phase (which combined an emulsifier and a colloid stabilizer) at 25° C. or below and with stirring typically at about 2000 rpm. Emulsification to the desired droplet size was achieved by increasing the stirrer speed to typically about 6000 rpm for an appropriate time. The resulting emulsion was then heated to about 50° C. for about 3–5 hours to form the microcapsules.

This experiment is summarized in the following Table 3:

TABLE 3

| Expt. | Acetal, g | TDI, g | PMPI, g | Herbicide, g | Mole Ratio TDI: Acetal |
|---|---|---|---|---|---|
| 9 | DD-BA, 8.28 | 3.72 | 0 | FPB, 63 | 3.87 |
| 10 | DD-BA, 8.28 | 3.72 | 0 | FPB, 63 | 3.87 |
| 11 | DDOD-BA, 8.28 | 3.72 | 0 | FPB, 63 | 4.87 |
| 12 | DDOD-BA, 8.4 | 3.75 | 0 | FPB, 63 | 4.84 |
| 13 | DDOD-BA, 8.33 | 3.90 | 0 | FPB, 63 | 5.07 |
| 14 | DDOD-BA, 8.23 | 3.72 | 0 | FPB, 63 | 4.90 |
| 15 | DDOD-BA, 9.47 | 4.35 | 1.74 | FPB, 93.36 | 5.48 |
| 16 | DDOD-BA, 8.23 | 3.72 | 0 | BUT, 47 | 4.90 |

The following procedure was used in examples 17–30:

In a vessel blanketed with nitrogen, a solution of dry/dewatered oligomeric acetal in the herbicide (butylate or fluazifop-p-butyl, as indicated) was added drop-wise to a solution of isomers of TDI in the herbicide, at a rate as to maintain the temperature of the reaction mixture between 20–25° C. Upon completion of the addition, the reaction mixture was heated to approximately 50° C. over a period of 10 to 15 minutes and maintained at 45 to 60° C. for an additional 20 to 70 minutes, typically 50 to 60 minutes. The resulting prepolymer solution was then cooled to room temperature in an ice bath.

A suspension of microcapsules containing the herbicide was prepared utilizing the Zeneca microencapsulation process of interfacial polymerization and condensation of a mixture of the prepolymer (prepared as described above) and isomers of polymethylene polyphenylisocyanate (PMPI). The organic phase was comprised of the herbicide, the prepolymer, and PMPI. The aqueous phase was comprised of Reax 100M (protective colloid) and a surfactant (Tergital) dissolved in water. An emulsion was then prepared by dispersing the oil phase in the aqueous phase employing a high shear stirrer until the desired particle size was achieved. The resulting oil in water emulsion was then heated to 50° C.±5° C. for three–six hours. In some cases, the resulting formulation was buffered and the pH adjusted to 10.

EXAMPLES 17–18

(TDI:Acetal=2.99:1)

A composition was prepared according to the foregoing procedure, in which 5.01 grams of DEG-BA was dissolved in 15.00 grams of butylate and 3.18 grams of TDI was dissolved in 10.03 grams of butylate. The DEG-BA solution was added drop-wise over a 10 minute period. Upon completion of the addition, the reaction vessel was heated to 50° C.±5° C. for 30 minutes. The resulting prepolymer solution was then used to prepare the microcapsule formulations having the following compositions:

| Example: | 17 Weight (g) | 18 Weight (g) |
|---|---|---|
| Prepolymer solution | 4.33 | 6.80 |
| PMPI | 0.93 | 0.46 |
| Butylate | 19.60 | 17.11 |
| Reax 100M (40% solution) | 1.31 | 1.31 |
| Tergital 15-S-7 (20% solution) | 0.41 | 0.41 |
| Water | 24.27 | 24.21 |
| Median Particle Size ($\mu$) | 10.5 | 10.5 |
| (PMPI:prepolymer) | (1:1) | (1:3) |

EXAMPLE 19

(TDI:Acetal=3.18:1; PMPI:prepolymer=1:8)

A composition was prepared according to the foregoing procedure, in which 5.00 grams of DEG-BA was dissolved in 15.04 grams of butylate and 3.38 grams of TDI was dissolved in 9.99 grams of butylate. The DEG-BA solution was added drop-wise over a 15 minute period. Upon completion of the addition, the reaction vessel was heated to 50° C.±5° C. for 60 minutes. The resulting prepolymer solution was then used to prepare a microcapsule formulation having the following composition: 4.66 grams prepolymer solution, 0.21 grams PMPI, 19.83 grams butylate, 1.33 grams Reax 100M (40% solution), 0.43 grams Tergitol 15-S-7 (20% solution) and 24.26 grams water. The median particle size was 7.4$\mu$.

EXAMPLE 20

(TDI:Acetal=2.99:1)

A composition was prepared according to the foregoing procedure, in which 8.02 grams of DEG-BA was dissolved in 23.99 grams of butylate and 5.09 grams of TDI was dissolved in 16.00 grams of butylate. The DEG-BA solution was added drop-wise over a 17 minute period. Upon completion of the addition, the reaction vessel was heated to 50° C.±5° C. for 50 minutes. The resulting prepolymer solution was then used to prepare the microcapsule formulations having the following compositions:

| | 20 Weight (g) |
|---|---|
| Prepolymer solution | 7.16 |
| PMPI | 0.32 |
| Butylate | 17.38 |
| Reax 100M (40% solution) | 1.34 |
| Tergital 15-S-7 (20% solution) | 0.43 |
| Water | 24.44 |
| Median Particle Size ($\mu$) | 2.9 |
| (PMPI:prepolymer) | (1:5) |

EXAMPLE 21

(TDI:Acetal=2.99:1)

A composition was prepared according to the foregoing procedure, in which 8.02 grams of DEG-BA was dissolved in 23.99 grams of butylate and 5.09 grams of TDI was dissolved in 16.00 grams of butylate. The DEG-BA solution was added dropwise over a 17 minute period. Upon completion of the addition, the reaction vessel was heated to 50° C.±5° C. for 50 minutes. The resulting prepolymer solution was then used to prepare the microcapsule formulations having the following compositions:

| Example: | Weight (g) |
|---|---|
| Prepolymer solution | 6.42 |
| PMPI | 0.45 |
| Butylate | 17.96 |
| Reax 100M (40% solution) | 1.34 |
| Tergital 15-S-7 (20% solution) | 0.43 |
| Water | 24.50 |
| Median Particle Size ($\mu$) | 2.9 |
| (PMPI:prepolymer) | (1:3) |

In Vitro Release Rate Evaluation

This composition was tested in vitro for release rate in the presence of acid as follows: 5.0 grams of formulation were diluted with 25.0 grams of water. Two 1.5 gram aliquots were removed, vacuum filtered onto 0.22 $\mu$m filter paper, and placed in a jar (to reduce volatilization of butylate) until the release rate measurement was performed. The remainder of the solution was treated with a concentrated solution of p-toluenesulfonic acid to pH 2.02. The acid treated solution was rolled for 10 minutes after which several 1.5 gram aliquots of the acid treated solution were removed, vacuum filtered onto 0.22 $\mu$m filter paper, and placed in a jar (to reduce volatilization butylate) until the release rate measurement was performed.

Release rate studies were conducted employing a Cahn RH electrobalance to monitor the rate of evaporative weight loss of butylate (a model compound with a high vapor pressure) from microcapsules under vacuum. The sample (on the filter paper) was placed on the sample pan of the electrobalance and allowed to equilibrate at 40° C. for 10–15 minutes in the sealed system prior to placing under vacuum. The weight loss, measured with the electrobalance enclosed under vacuum, was recorded on a chart recorder.

TABLE 4

| Exposure Time (Hrs)* | Release Rate (mg/min) Trial 1 | Release Rate (mg/min) Trial 2 |
|---|---|---|
| 1 (untreated) | 7.5 | 6.8 |
| 8 (untreated) | 9.6 | 10.7 |
| 1 | 12.3 | 12.0 |
| 2 | 10.7 | 13.3 |
| 3 | 14.2 | 15.6 |
| 4 | — | 12.1 |
| 6 | 17.1 | 16.4 |
| 7 | 16.0 | — |
| 8 | 20.3 | 14.9 |
| 24 | 16.0 | — |

*Exposure time is defined as time between addition of acid and release rate measurement.
Note:
The release rate of non-encapsulated butylate was determined to be about 17–19 mg/min.

EXAMPLES 22–25

(TDI:Acetal=4.99:1)

A composition was prepared according to the foregoing procedure, in which 8.03 grams of DEG-BA was dissolved in 24.02 grams of butylate and 8.50 grams of TDI was dissolved in 16.00 grams of butylate. The DEG-BA solution was added drop-wise over a 17 minute period. Upon completion of the addition, the reaction vessel was heated to 55° C.±5° C. for 70 minutes. The resulting prepolymer solution was then used to prepare the microcapsule formulations having the following compositions:

| Example: | 22 Weight (g) | 23 Weight (g) | 24 Weight (g) | 25 Weight (g) |
|---|---|---|---|---|
| Prepolymer solution | 7.58 | 6.84 | 4.56 | 8.10 |
| PMPI | 0.32 | 0.47 | 0.91 | 0.23 |
| Butylate | 16.99 | 17.54 | 19.35 | 6.55 |
| Reax 100M (40% solution) | 1.34 | 1.32 | 1.33 | 1.33 |
| Tergital 15-S-7 (20% solution) | 0.44 | 0.46 | 0.43 | 0.43 |
| Water | 24.57 | 25.67 | 24.53 | 24.31 |
| Median Particle Size ($\mu$) | 2.9 | 9.1 | 3.2 | 2.9 |
| (PMPI:prepolymer) | (1:5) | (1:3) | (1:1) | (1:8) |

EXAMPLES 26–27

(TDI:Acetal=2.98:1)

A composition was prepared according to the foregoing procedure, in which 5.03 grams of DEG-BA was dissolved in 15.32 grams of fluazifop-p-butyl and 3.18 grams of TDI was dissolved in 10.03 grams of fluazifop-p-butyl. The DEG-BA solution was added drop-wise over a 10 minute period. Upon completion of the addition, the reaction vessel was heated to 50° C.±5° C. for 50 minutes. The resulting prepolymer solution was then used to prepare the microcapsule formulations having the following compositions:

| Example: | 26 Weight (g) | 27 Weight (g) |
|---|---|---|
| Prepolymer solution | 8.53 | 17.06 |
| PMPI | 0.60 | 1.20 |
| fluazifop-p-butyl | 22.87 | 14.36 |
| Reax 100M (40% solution) | 1.87 | 1.89 |
| Tergital XD (20% solution) | 3.74 | 3.95 |
| Water | 24.00 | 23.67 |
| $NaCO_3 \cdot H_2O$ | 0.36 | 0.36 |
| NaOH (25% solution) | to pH 10 | to pH 10 |
| Median Particle Size ($\mu$) | 5.6 | 4.8 |
| (PMPI:prepolymer) | (1:3) | (1:3) |

EXAMPLES 28–29

(TDI:Acetal=3.09:1)

A composition was prepared according to the foregoing procedure, in which 5.04 grams of DEG-BA was dissolved in 15.03 grams of fluazifop-p-butyl and 3.30 grams of TDI was dissolved in 9.99 grams of fluazifop-p-butyl. The DEG-BA solution was added drop-wise over a 13 minute period. Upon completion of the addition, the reaction vessel was heated to 50° C.±5° C. for 50 minutes. The resulting prepolymer solution was then used to prepare the microcapsule formulations having the following compositions:

| Example: | 28 Weight (g) | 29 Weight (g) |
|---|---|---|
| Prepolymer solution | 7.28 | 9.53 |
| PMPI | 0.91 | 1.23 |
| fluazifop-p-butyl | 23.94 | 21.28 |
| Reax 100M (40% solution) | 1.89 | 1.87 |
| Tergital XD (20% solution) | 3.73 | 3.73 |
| Water | 23.98 | 24.29 |
| $NaCO_3 \cdot H_2O$ | 0.33 | 0.33 |
| NaOH (25% solution) | to pH 10 | to pH 10 |

-continued

| Example: | 28 Weight (g) | 29 Weight (g) |
|---|---|---|
| Median Particle Size (μ) (PMPI:prepolymer) | 9.4 (1:1.68) | 12.9 (1:1.68) |

EXAMPLES 30–31
(TDI:Acetal=4.94:1)

A composition was prepared according to the foregoing procedure, in which 5.04 grams of DEG-BA was dissolved in 15.02 grams of fluazifop-p-butyl and 5.28 grams of TDI was dissolved in 10.02 grams of fluazifop-p-butyl. The DEG-BA solution was added dropwise over a 17 minute period. Upon completion of the addition, the reaction vessel was heated to 50° C.±5° C. for 50 minutes. The resulting prepolymer solution was then used to prepare the microcapsule formulations having the following compositions:

| Example: | 30 Weight (g) | 31 Weight (g) |
|---|---|---|
| Prepolymer solution | 7.50 | 10.01 |
| PMPI | 0.94 | 1.19 |
| fluazifop-p-butyl | 23.62 | 20.78 |
| Reax 100M (40% solution) | 1.88 | 1.88 |
| Tergital XD (20% solution) | 3.76 | 3.75 |
| Water | 24.18 | 24.11 |
| NaCO₃ · H₂O | 0.33 | 0.33 |
| NaOH (25% solution) | to pH 10.1 | to pH 10 |
| Median Particle Size (μ) (PMPI:prepolymer) | 12.0 (1:1.6) | 12.7 (1:1.7) |

Biological Evaluation

Biological evaluation of acid sensitive microcapsules containing the herbicide fluazifop-P-butyl was performed, in comparison with a similar microcapsule not treated with acid and a commercial non-encapsulated formulation of this herbicide sold under the trademark Fusilade® DX®. The samples were evaluated by diluting with water and forming spray solutions and were applied at four different rates: 0.0156, 0.0313, 0.0625 and 0.125 pounds/acre (0.0175, 0.0351, 0.0704, and 0.140 kg/ha). The solutions were applied to flats containing five grassy weeds: crabgrass (*Echinochloa crusgalli*), giant foxtail (*Setaria faberi*), green foxtail (*Setaria viridis*), yellow foxtail (*Setaria lutescens*) and broadleaf signalgrass (*Brachiaria platyphylla*). Three samples of microcapsules prepared according to Example 29 were included in these tests. All samples of microcapsules were prepared in the same manner and had the same properties, namely:

| Weight percent herbicide | 42 |
|---|---|
| Mole Ratio PMPI/prepolymer | 1.74:1 |
| Particle size | 12.9 μm |
| Wall content, weight percent | 10.1 |

Crop oil concentrate was added at 1% to all sprayed solutions. Acid solution controls not containing a herbicide were also run to confirm that the acid itself did not contribute to the control of the weeds. This was confirmed by the tests. The microcapsules of the present invention were sprayed in three ways: without acid (test A), treated with p-toluenesulfonic acid at pH of 1.52 (test B) and treated with p-toluenesulfonic acid at pH 1.02 (test C).

The results of these tests are tabulated in the following Table 4:

TABLE 4

| Test Sample | Acid, pH | Average Weed Control, % (7 Days) |
|---|---|---|
| A | — | 29.75 |
| B | 1.02 | 47.5 |
| C | 1.52 | 51.0 |
| Fusilade ®DX ® | — | 65.25 |

The acid solution controls showed little or no weed control indicating that the acid itself does not materially affect these test results. The weeds sprayed with the acid solution at pH approximately 1.0 appeared to have some leaf burn.

Similar tests were conducted utilizing microcapsules prepared according to Example 31 wherein which the TDI/diol ratio was 5:1. The acid was utilized at a higher pH of 1.5–2. Some tests included the use of polyethylene glycol (PEG 400) as a humectant. The results of these tests are shown in the following Table 5.

TABLE 5

| Test Sample | Acid, pH | PEG 400 (1%) | Average Weed Control, % (14 Days) |
|---|---|---|---|
| D | — | No | 36 |
| E | — | Yes | 63 |
| F | 2.07 | No | 50 |
| G | 2.05 | Yes | 67 |
| H | 1.52 | Yes | 66 |
| Fusilade ® DX ® | — | No | 82 |

What is claimed is:

1. A microcapsule formed of a polyurea shell wall and an encapsulated ingredient or ingredients enclosed within the shell wall, the wall comprising at least one oligomeric acetal moiety.

2. A microcapsule according to claim 1 in which the oligomeric acetal moiety is one which is hydrolyzed under exposure to acidic conditions.

3. A microcapsule according to claim 1 in which the oligomeric acetal moiety has the formula

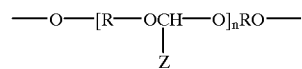

in which R is (a) a moiety containing a chain of from 5 to about 40 optionally substituted carbon atoms, (b) a moiety containing a chain of from 4 to about 40 carbon atoms and one or more internally linked oxygen or sulfur atoms or —NH— groups, or (c) an optionally substituted ethylene or propylene moiety; Z is (a) an optionally substituted phenyl group; (b) an optionally substituted $C_1$–$C_{20}$ alkyl, $C_2$–$C_{20}$ alkenyl, $C_3$–$C_8$ cycloalkyl or $C_5$–$C_8$ cycloalkenyl group; or benzoyl; and n is 1 if R is (a) or (b), or is 2–20 if R is (c).

4. A microcapsule according to claim 2 in which is stable under basic conditions.

5. A microcapsule according to claim 3 which is stable under basic conditions.

6. A microcapsule according to claim 3 in which R is a $C_5$–$C_{40}$ alkyl or a group having the formula —$CH_2$—$R_2$—$CH_2$ in which R2 is an optionally substituted phenyl or $C_5$–$C_{15}$ cycloalkyl or cycloalkenyl ring and the methylene groups are situated no closer than the 1, 3 positions on the ring.

7. A microcapsule according to claim 3 in which the microcapsule shell wall contains the moiety

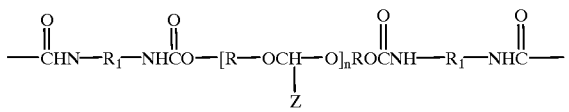

in which $R_1$ is an aliphatic or aromatic moiety.

8. A microcapsule according to claim 3 or 7 in which R is an optionally substituted alkyl group having from 5 to about 40 carbon atoms and n is 1.

9. A microcapsule according to claim 3 or 7 in which R is an optionally substituted alkyl group having from 5 to about 30 carbon atoms and n is 1.

10. A microcapsule according to claim 3 or 7 in which R is an optionally substituted alkyl group having from 8 to about 20 carbon atoms and n is 1.

11. A microcapsule according to claim 3 or 7 in which R is $C_2$–$C_3$ alkyl and n is a value of from 2 to about 20.

12. A microcapsule according to claim 3 or 7 in which R is $C_2$–$C_3$ alkyl and n is a value of from 2 to about 4.

13. A microcapsule according to claim 3 or 7 in which Z is an optionally substituted phenyl group.

14. A microcapsule according to claim 3 or 7 in which R is a group having the formula —$CH_2$—$R_2$—$CH_2$, wherein $R_2$ is optionally substituted phenyl or $C_5$–$C_{15}$ cycloalkyl or cycloalkenyl, in which the methylene groups are substituted at least three carbon atoms apart on the ring.

15. A microcapsule according to claim 14 in which R2 is an optionally substituted phenyl or C5–C15 cycloalkyl or cycloalkenyl ring.

16. A microcapsule according to claim 3 or 7 in which Z is unsubstituted phenyl.

17. A microcapsule according to claim 1 in which the encapsulated ingredient comprises an agricultural chemical.

18. A microcapsule according to claim 1 in which the encapsulated ingredient comprises a pesticide.

19. A microcapsule according to claim 1 in which the encapsulated ingredient comprises one or more herbicides.

20. A microcapsule according to claim 1 in which the encapsulated ingredient comprises one or more insecticides.

21. A microcapsule according to claim 1 in which the shell wall further comprises a moiety which generates acid when exposed to light.

\* \* \* \* \*